United States Patent [19]
Murphy et al.

[11] Patent Number: 5,877,001
[45] Date of Patent: Mar. 2, 1999

[54] AMIDASE

[75] Inventors: Dennis Murphy, Paoli; John Reid, Bryn Mawr, both of Pa.; Dan Robertson, Haddonfield, N.J.

[73] Assignee: Diverso Corporation, San Diego, Calif.

[21] Appl. No.: 664,646

[22] Filed: Jun. 17, 1996

[51] Int. Cl.$^6$ .............................. C12N 9/78; C12N 1/20; C12P 21/06; C07H 21/02

[52] U.S. Cl. .................. 435/227; 435/252.3; 435/320.1; 435/69.1; 435/228; 435/230; 536/23.1; 536/23.2; 536/23.7; 530/350

[58] Field of Search ..................................... 435/227, 228, 435/230, 69.1, 252.33, 320.1; 536/23.2, 23.7; 530/350

[56] References Cited

U.S. PATENT DOCUMENTS 5,451,522  9/1995  Queener et al. ...................... 435/252.3
5,494,796  2/1996  Spears et al. ............................... 435/6

*Primary Examiner*—Rebecca E. Prouty
*Assistant Examiner*—Tekchand Saidha
*Attorney, Agent, or Firm*—Fish & Richardson P.C.

[57] ABSTRACT

A purified thermostable enzyme is derived from the archael bacterium Thermococcus GU5L5. The enzyme has a molecular weight of about 68.5 kilodaltons and has cellulase activity. The enzyme can be produced from native or recombinant host cells and can be used for the removal of arginine, phenylalanine, or methionine amino acids from the N-terminal end of peptides in peptide or peptidomimetic synthesis. The enzyme is selective for the L, or 'natural' enantiomer of the amino acid derivatives and is therefore useful for the production of optically active compounds. These reactions can be performed in the presence of the chemically more reactive ester functionality, a step which is very difficult to achieve with nonenzymatic methods.

10 Claims, 6 Drawing Sheets

Thermococcus GU5L5 Amidase

1    ATG ACC GGC ATC GAA TGG AAC CAC GAG ACC TTT TCT AAG TTC GCC TAC CTG GGC GAC CCG   60
1    Met Thr Gly Ile Glu Trp Asn His Glu Thr Phe Ser Lys Phe Ala Tyr Leu Gly Asp Pro   20

61   AGG ATA CGG GGA AAC TTA ATC GCG TAC ACC CTG ACG AAG GCC AAC ATG AAG GAC AAC AAG
                                                                                      120
21   Arg Ile Arg Gly Asn Leu Ile Ala Tyr Thr Leu Thr Lys Ala Asn Met Lys Asp Asn Lys   40

121  TAC GAG AGC ACG GTT GTT GTT GAA GAC CTT GAA ACG GGC TCA AGG CGC TTC ATC GAG AAC   180
41   Tyr Glu Ser Thr Val Val Val Glu Asp Leu Glu Thr Gly Ser Arg Arg Phe Ile Glu Asn   60

181  GCC TCA ATG CCG AGG ATT TCG CCA GAC GGC AGA AAG CTC GCC TTC ACC TGC TTT AAC GAG   240
61   Ala Ser Met Pro Arg Ile Ser Pro Asp Gly Arg Lys Leu Ala Phe Thr Cys Phe Asn Glu   80

241  GAG AAG AAG GAG ACC GAG ATA TGG GTG GCC GAT ATC CAG ACC CTG AGC GCC AAG AAA GTC
                                                                                      300
81   Glu Lys Lys Glu Thr Glu Ile Trp Val Ala Asp Ile Gln Thr Leu Ser Ala Lys Lys Val   100

FIG. 1A

301 CTC TCA ACT AAA AAC GTC CGC TCG ATG CAG TGG AAC GAC GAT TCA AGG AGA CTC TTA GTT   360
101 Leu Ser Thr Lys Asn Val Arg Ser Met Gln Trp Asn Asp Asp Ser Arg Arg Leu Leu Val   120

361 GTC GGC TTC AAG AGG AGG GAC GAT GAG GAC TTC GTC TTT GAC GAC GTC CCG GTC TGG   420
121 Val Gly Phe Lys Arg Arg Asp Asp Glu Asp Phe Val Phe Asp Asp Val Pro Val Trp   140

421 TTC GAC AAT ATG GGA TTC TTT GAT GGA GAG AAG ACG ACG TTC TGG GTT CTT GAC ACT GAG   480
141 Phe Asp Asn Met Gly Phe Phe Asp Gly Glu Lys Thr Thr Phe Trp Val Leu Asp Thr Glu   160

481 GCC GAG GAG ATA ATC GAG CAG TTC GAG AAG CCG AGG TTT TCG AGT GGC CTC TGG CAC GGC   540
161 Ala Glu Glu Ile Ile Glu Gln Phe Glu Lys Pro Arg Phe Ser Ser Gly Leu Trp His Gly   180

541 GAT GCG ATA GTT GTG AAC GTC CCG CAC CGC GAG GGG AGC AAG CCT GCC CTG TTC AAG TTC   600
181 Asp Ala Ile Val Val Asn Val Pro His Arg Glu Gly Ser Lys Pro Ala Leu Phe Lys Phe   200

601 TAC GAC ATA GTC CTA TGG AAG GAC GGG GAG GAA GAG AAG CTC TTC GAG AGG GTC TCC TTC   660
201 Tyr Asp Ile Val Leu Trp Lys Asp Gly Glu Glu Lys Leu Phe Glu Arg Val Ser Phe   220

661 GAG GCG GTT GAC TCC GAC GGA AAG AGA ATA CTC CTG AGG GGC AAG AAA AAA AAG CGG TTC
720
221 Glu Ala Val Asp Ser Asp Gly Lys Arg Ile Leu Leu Arg Gly Lys Lys Lys Lys Arg Phe   240

FIG. 1B

```
721  ATC AGC GAG CAC GAC TGG CTG TAC CTC TGG GAC GGC GAG CTT AAA CCG ATC TAC GAG GGC  780
241  Ile Ser Glu His Asp Trp Leu Tyr Leu Trp Asp Gly Glu Leu Lys Pro Ile Tyr Glu Gly   260

781  CCG CTC GAC GTC TGG GAA GCC AAG CTC ACG GAA GGA AAG GTC TAC TTC CTC ACT CCA GAT  840
261  Pro Leu Asp Val Trp Glu Ala Lys Leu Thr Glu Gly Lys Val Tyr Phe Leu Thr Pro Asp   280

841  GCG GGC AGG GTA AAC CTC TGG CTC TGG GAC GGG AAG GCC GAG CGT GTT GTT ACC GGC GAC  900
281  Ala Gly Arg Val Asn Leu Trp Leu Trp Asp Gly Lys Ala Glu Arg Val Val Thr Gly Asp   300

901  CAC TGG ATT TAC GGG CTT GAC GTC AGC GAT GGC AAA GCA TTG CTC CTC ATC ATG ACC GCC  960
301  His Trp Ile Tyr Gly Leu Asp Val Ser Asp Gly Lys Ala Leu Leu Leu Ile Met Thr Ala   320

961  ACG AGG ATA GGC GAG CTC TAC CTC TAC GAC GGC GAG CTG AAA CAG GTC ACC GAA TAC AAC
321  Thr Arg Ile Gly Glu Leu Tyr Leu Tyr Asp Gly Glu Leu Lys Gln Val Thr Glu Tyr Asn   340
1020

1021 GGG CCG ATA TTC AGG AAG CTC AAG ACC TTC GAG CCG AGG CAC TTC CGC TTC AAG AGC AAA
341  Gly Pro Ile Phe Arg Lys Leu Lys Thr Phe Glu Pro Arg His Phe Arg Phe Lys Ser Lys   360
1080

1081 GAC CTC GAG ATA GAC GGC TGG TAC CTC AGG CCG GAG GTT AAA GAG GAG AAG GCC CCG GTG
361  Asp Leu Glu Ile Asp Gly Trp Tyr Leu Arg Pro Glu Val Lys Glu Glu Lys Ala Pro Val   380
1140
```

FIG. 1C

```
1141  ATA GTC TTC GTC CAC GGC GGG CCG AAG GGC ATG TAC GGA CAC CGC TTC GTC TAC GAG ATG
                                                                                    1200
 381  Ile Val Phe Val His Gly Gly Pro Lys Gly Met Tyr Gly His Arg Phe Val Tyr Glu Met  400

1201  CAG CTG ATG GCG AGC AAG GGC TAC TAC GTC GTC TTC GTG AAC CCG CGC GGC AGC GAC GGC
                                                                                    1260
 401  Gln Leu Met Ala Ser Lys Gly Tyr Tyr Val Val Phe Val Asn Pro Arg Gly Ser Asp Gly  420

1261  TAT AGC GAA GAC TTC GCG CTC CGC GTC CTG GAG AGG ACT GGC TTG GAG GAC TTT GAG GAC
                                                                                    1320
 421  Tyr Ser Glu Asp Phe Ala Leu Arg Val Leu Glu Arg Thr Gly Leu Glu Asp Phe Glu Asp  440

1321  ATA ATG AAC GGC ATC GAG GAG TTC TTC AAG CTC GAA CCG CAG GCC GAC AGG GAG CGC GTT
                                                                                    1380
 441  Ile Met Asn Gly Ile Glu Glu Phe Phe Lys Leu Glu Pro Gln Ala Asp Arg Glu Arg Val  460

1381  GGA ATA ACG GGC ATA AGC TAC GGC GGC TTC ATG ACC AAC TGG GCC TTG ACT CAG AGC GAC
                                                                                    1440
 461  Gly Ile Thr Gly Ile Ser Tyr Gly Gly Phe Met Thr Asn Trp Ala Leu Thr Gln Ser Asp  480

1441  CTC TTC AAG GCA GGA ATA AGC GAG AAC GGC ATA AGC TAC TGG CTC ACC AGC TAC GCC TTC
                                                                                    1500
 481  Leu Phe Lys Ala Gly Ile Ser Glu Asn Gly Ile Ser Tyr Trp Leu Thr Ser Tyr Ala Phe  500
```

FIG. 1D

1501 TCG GAC ATA GGG CTC TGG TAC GAC GTC GAG GTC ATC GGG CCA AAT CCG TTA GAG AAC GAG 1560
501  Ser Asp Ile Gly Leu Trp Tyr Asp Val Glu Val Ile Gly Pro Asn Pro Leu Glu Asn Glu  520

1561 AAC TTC AGG AAG CTC AGC CCG CTG TTC TAC GCT CAG AAC GTG AAG GCG CCG ATA CTC CTA 1620
521  Asn Phe Arg Lys Leu Ser Pro Leu Phe Tyr Ala Gln Asn Val Lys Ala Pro Ile Leu Leu  540

1621 ATC CAC TCG CTT GAG GAC TAC CGC TGT CCG CTC GAC CAG AGC CTT ATG TTC TAC AAC GTG 1680
541  Ile His Ser Leu Glu Asp Tyr Arg Cys Pro Leu Asp Gln Ser Leu Met Phe Tyr Asn Val  560

1681 CTC AAG GAC ATG GGC AAG GAA GCC TAC ATA GCG ATA TTC AAG CGC GGC GCC CAC GGC CAC 1740
561  Leu Lys Asp Met Gly Lys Glu Ala Tyr Ile Ala Ile Phe Lys Arg Gly Ala His Gly His  580

1741 AGC GTC CGG GGA AGC CCG AGG CAC AGG CCG AAG CGC TAC AGG CTC TTC ATA GAG TTC TTC 1800
581  Ser Val Arg Gly Ser Pro Arg His Arg Pro Lys Arg Tyr Arg Leu Phe Ile Glu Phe Phe  600

1801 GAG CGC AAG CTC AAG AAG TAC GAG GAG GGC TTT GAG GTA GAG AAG ATA CTC AAG GGG AAT 1860
601  Glu Arg Lys Leu Lys Lys Tyr Glu Glu Gly Phe Glu Val Glu Lys Ile Leu Lys Gly Asn  620

1861 GGG AAC TGA  1869
621  Gly Asn End  623

FIG. 1E

AMIDASE

BACKGROUND OF THE INVENTION

This invention relates to newly identified polynucleotides, polypeptides encoded by such polynucleotides, the use of such polynucleotides and polypeptides, as well as the production and isolation of such polynucleotides and polypeptides. More particularly, the polypeptide of the present invention has been identified as an amidase and in particular an enzyme having activity in the removal of arginine, phenylalanine or methionine from the N-terminal end of peptides in peptide or peptidomimetic synthesis.

Thermophilic bacteria have received considerable attention as sources of highly active and thermostable enzymes (Bronneomeier, K. and Staudenbauer, W. L., D. R. Woods (Ed.), The Clostridia and Biotechnology, Butterworth Publishers, Stoneham, Mass. (1993). Recently, the most extremely thermophilic organotrophic eubacteria presently known have been isolated and characterized. These bacteria, which belong to the genus Thermotoga, are fermentative microorganisms metabolizing a variety of carbohydrates (Huber, R. and Stetter, K. O., in Ballows, et al., (Ed.), The Procaryotes, 2nd Ed., Springer-Verlaz, N.Y., pgs. 3809–3819 (1992)).

Because to date most organisms identified from the archaeal domain are thermophiles or hyperthermophiles, archaeal bacteria are also considered a fertile source of thermophilic enzymes.

In accordance with one aspect of the present invention, there is provided a novel enzyme, as well as active fragments, analogs and derivatives thereof.

In accordance with another aspect of the present invention, there are provided isolated nucleic acid molecules encoding an enzyme of the present invention including mRNAs, DNAs, cDNAs, genomic DNAs as well as active analogs and fragments of such enzymes.

In accordance with yet a further aspect of the present invention, there is provided a process for producing such a polypeptide by recombinant techniques comprising culturing recombinant prokaryotic and/or eukaryotic host cells, containing a nucleic acid sequence encoding an enzyme of the present invention, under conditions promoting expression of said enzyme and subsequent recovery of said enzyme.

In accordance with yet a further aspect of the present invention, there is provided a process for utilizing such enzyme, or polynucleotide encoding such enzyme. The enzyme is useful for the removal of arginine, phenylalanine, or methionine amino acids from the N-terminal end of peptides in peptide or peptidomimetic synthesis. The enzyme is selective for the L, or "natural" enantiomer of the amino acid derivatives and is therefore useful for the production of optically active compounds. These reactions can be performed in the presence of the chemically more reactive ester functionality, a step which is very difficult to achieve with nonenzymatic methods. The enzyme is also able to tolerate high temperatures (at least 70° C.), and high concentrations of organic solvents (>40% DMSO), both of which cause a disruption of secondary structure in peptides; this enables cleavage of otherwise resistant bonds.

In accordance with yet a further aspect of the present invention, there is also provided nucleic acid probes comprising nucleic acid molecules of sufficient length to specifically hybridize to a nucleic acid sequence of the present invention.

In accordance with yet a further aspect of the present invention, there is provided a process for utilizing such enzymes, or polynucleotides encoding such enzymes, for in vitro purposes related to scientific research, for example, to generate probes for identifying similar sequences which might encode similar enzymes from other organisms.

These and other aspects of the present invention should be apparent to those skilled in the art from the teachings herein.

The following drawings are illustrative of embodiments of the invention and are not meant to limit the scope of the invention as encompassed by the claims.

FIG. 1 is an illustration of the full-length DNA and corresponding deduced amino acid sequence of the enzyme of the present invention. Sequencing was performed using a 378 automated DNA sequencer (Applied Biosystems, Inc.).

Figure 3:
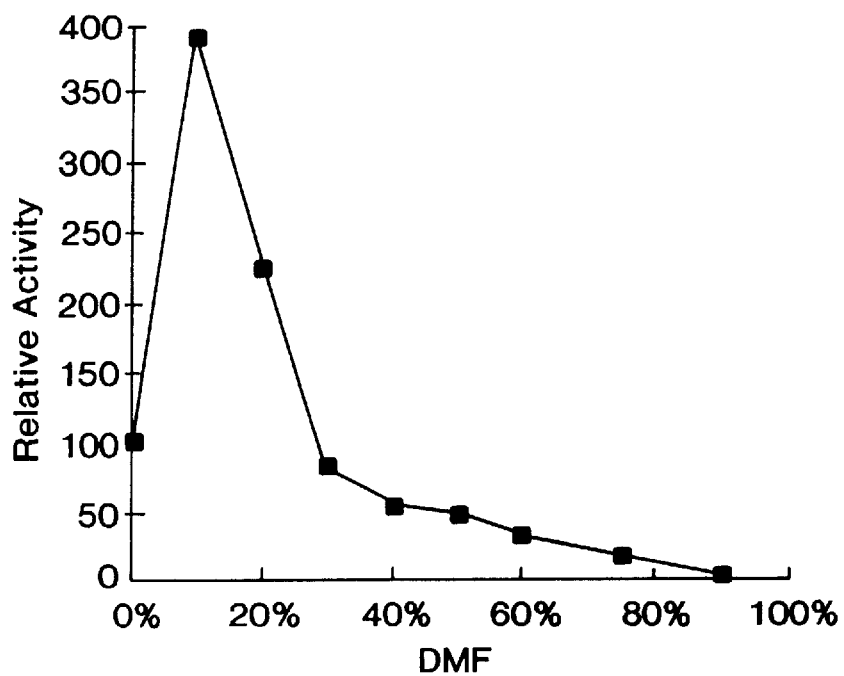

FIG. 3 shows the relative initial linear rates (increase in fluorescence per min. i.e. "activity") versus concentration of DMF for the more reactive CBZ-L-arg-AMC, from The term "gene" means the segment of DNA involved in producing a polypeptide chain; it includes regions preceding and following the coding region (leader and trailer) as well as intervening sequences (introns) between individual coding segments (exons).

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

"Recombinant" enzymes refer to enzymes produced by recombinant DNA techniques; i.e., produced from cells transformed by an exogenous DNA construct encoding the desired enzyme. "Synthetic" enzymes are those prepared by chemical synthesis.

A DNA "coding sequence of" or a "nucleotide sequence encoding" a particular enzyme, is a DNA sequence which is transcribed and translated into an enzyme when placed under the control of appropriate regulatory sequences. A "bpromotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

The present invention provides a purified thermostable enzyme that catalyzes the removal of arginine, phenylalanine, or methionine amino acids from the N-terminal end of peptides in peptide or peptidomimetic synthesis. The purified enzyme is an amidase derived from an organism referred to herein as "Thermococcus GU5L5" which is a thermophilic archaeal organism which has a very high temperature optimum. The organism is strictly anaerobic and grows between 55° and 90° C. (optimally at 85° C.). GU5L5 was discovered in a shallow marine hydrothermal area in Vulcano, Italy. The organism has coccoid cells occurring in singlets or pairs. GU5L5 grows optimally at 85° C. and pH 6.0 in a marine medium with peptone as a substrate and nitrogen in gas phase.

The polynucleotide of this invention was originally recovered from a genomic gene library derived from Thermococcus GU5L5 as described below. It contains an open reading frame encoding a protein of 622 amino acid residues.

In a preferred embodiment, the amidase enzyme of the present invention has a molecular weight of about 68.5 kilodaltons as inferred from the nucleotide sequence of the gene.

In accordance with an aspect of the present invention, there are provided isolated nucleic acid molecules (polynucleotides) which encode for the mature enzyme having the deduced amino acid sequence of FIG. 1 (SEQ ID NO:2).

This invention, in addition to the isolated nucleic acid molecule encoding an amidase enzyme disclosed in FIG. 1 (SEQ ID NO: 1), also provides substantially similar sequences. Isolated nucleic acid sequences are substantially similar if: (i) they are capable of hybridizing under stringent conditions, hereinafter described, to SEQ ID NO: 1; or (ii) they encode DNA sequences which are degenerate to SEQ ID NO: 1. Degenerate DNA sequences encode the amino acid sequence of SEQ ID NO:2,but have variations in the nucleotide coding sequences. As used herein, "substantially similar" refers to the sequences having similar identity to the sequences of the instant invention. The nucleotide sequences that are substantially similar can be identified by hybridization or by sequence comparison. Enzyme sequences that are substantially similar can be identified by one or more of the following: proteolytic digestion, gel electrophoresis and/or microsequencing.

One means for isolating a nucleic acid molecule encoding an amidase enzyme is to probe a gene library with a natural or artificially designed probe using art recognized procedures (see, for example: Current Protocols in Molecular Biology, Ausubel F. M. et al. (EDS.) Green Publishing Company Assoc. and John Wiley Interscience, N.Y., 1989, 1992). It is appreciated to one skilled in the art that SEQ ID NO: 1, or fragments thereof (comprising at least 15 contiguous nucleotides), is a particularly useful probe. Other particular useful probes for this purpose are hybridizable fragments to the sequences of SEQ ID NO: 1 (i.e., comprising at least 15 contiguous nucleotides).

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acid is first prehybridized for 30 minutes at 45° C. in a solution consisting of 0.9M NaCl, 50 mM NaH$_2$PO$_4$, pH 7.0, 5.0 mM Na$_2$EDTA, 0.5% SDS, 10× Denhardt's, and 0.5 mg/mL polyriboadenylic acid. Approximately 2×10$^7$ cpm (specific activity 4–9 ×10$^8$ cpm/ug) of $^{32}$P end-labeled oligonucleotide probe are then added to the solution. After 12–16 hours of incubation, the membrane is washed for 30 minutes at room temperature in 1× SET (150 mM NaCl, 20 mM Tris hydrochloride, pH 7.8, 1 mM Na$_2$EDTA) containing 0.5% SDS, followed by a 30 minute wash in fresh 1× SET at Tm-10° C. for the oligo-nucleotide probe. The membrane is then exposed to auto-radiographic film for detection of hybridization signals.

Stringent conditions means hybridization will occur only if there is at least 90% identity, preferably at least 95% identity and most preferably at least 97% identity between the sequences. See J. Sambrook et al., Molecular Cloning, A Laboratory Manual (2d Ed. 1989) (Cold Spring Harbor Laboratory) which is hereby incorporated by reference in its entirety.

"Identity" as the term is used herein, refers to a polynucleotide sequence which comprises a percentage of the same bases as a reference polynucleotide (SEQ ID NO: 1). For example, a polynucleotide which is at least 90% identical to a reference polynucleotide, has polynucleotide bases which are identical in 90% of the bases which make up the reference polynucleotide and may have different bases in 10% of the bases which comprise that polynucleotide sequence.

The present invention also relates to polynucleotides which differ from the reference polynucleotide such that the changes are silent changes, for example the changes do not alter the amino acid sequence encoded by the polynucleotide. The present invention also relates to nucleotide changes which result in amino acid substitutions, additions, deletions, fusions and truncations in the enzyme encoded by the reference polynucleotide (SEQ ID NO: 1). In a preferred aspect of the invention these enzymes retain the same biological action as the enzyme encoded by the reference polynucleotide.

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other animal sources or to screen such sources for related sequences.

The coding sequence for the amidase enzyme of the present invention was identified by preparing a Thenmococcus GU5L5 genomic DNA library and screening the library for the clones having amidase activity. Such methods for constructing a genomic gene library are well-known in the art. One means, for example, comprises shearing DNA isolated from GU5L5 by physical disruption. A small amount of the sheared DNA is checked on an agarose gel to verify that the majority of the DNA is in the desired size range (approximately 3–6 kb). The DNA is then blunt ended using Mung Bean Nuclease, incubated at 37° C. and phenol/chloroform extracted. The DNA is then methylated using Eco RI Methylase. Eco R1 linkers are then ligated to the blunt ends through the use of T4 DNA ligase and incubation at 4° C. The ligation reaction is then terminated and the DNA is cut-back with Eco R1 restriction enzyme. The DNA is then size fractionated on a sucrose gradient following procedures known in the art, for example, Maniatis, T., et al., *Molecular Cloning*, Cold Spring Harbor Press, N.Y., 1982, which is hereby incorporated by reference in its entirety.

A plate assay is then performed to get an approximate concentration of the DNA. Ligation reactions are then performed and 1 μof the ligation reaction is packaged to construct a library. Packaging, for example, may occur through the use of purified λgt11 phage arms cut with EcoRi and DNA cut with EcoRI after attaching EcoRI linkers. The DNA and λgt11 arms are ligated with DNA ligase. The ligated DNA is then packaged into infectious phage particles. The packaged phages are used to infect *E. coli* cultures and the infected cells are spread on agar plates to yield plates carrying thousands of individual phage plaques. The library is then amplified.

Fragments of the full length gene of the present invention may be used as a hybridization probe for a cDNA or a genomic library to isolate the full length DNA and to isolate other DNAs which have a high sequence similarity to the gene or similar biological activity. Probes of this type have at least 10, preferably at least 15, and even more preferably at least 30 bases and may contain, for example, at least 50 or more bases. The probe may also be used to identify a DNA clone corresponding to a full length transcript and a genomic clone or clones that contain the complete gene including regulatory and promotor regions, exons, and introns.

The isolated nucleic acid sequences and other enzymes may then be measured for retention of biological activity characteristic to the enzyme of the present invention, for example, in an assay for detecting enzymatic amidase activity. Such enzymes include truncated forms of amidase, and variants such as deletion and insertion variants.

The polynucleotide of the present invention may be in the form of DNA which DNA includes cDNA, genomic DNA, and synthetic DNA. The DNA may be double-stranded or single-stranded, and if single stranded may be the coding strand or non-coding (anti-sense) strand. The coding sequence which encodes the mature enzyme may be identical to the coding sequence shown in FIG. 1 (SEQ ID NO: 1) and/or that of the deposited clone or may be a different coding sequence which coding sequence, as a result of the redundancy or degeneracy of the genetic code, encodes the same mature enzyme as the DNA of FIG. 1 (SEQ ID NO: 1).

The polynucleotide which encodes for the mature enzyme of FIG. 1 (SEQ ID NO:2) may include, but is not limited to: only the coding sequence for the mature enzyme; the coding sequence for the mature enzyme and additional coding sequence such as a leader sequence or a proprotein sequence; the coding sequence for the mature enzyme (and optionally additional coding sequence) and non-coding sequence, such as introns or non-coding sequence 5' and/or 3' of the coding sequence for the mature enzyme.

Thus, the term "polynucleotide encoding an enzyme (protein)" encompasses a polynucleotide which includes only coding sequence for the enzyme as well as a polynucleotide which includes additional coding and/or non-coding sequence.

The present invention further relates to variants of the hereinabove described polynucleotides which encode for fragments, analogs and derivatives of the enzyme having the deduced amino acid sequence of FIG. 1 (SEQ ID NO:2). The variant of the polynucleotide may be a naturally occurring allelic variant of the polynucleotide or a non-naturally occurring variant of the polynucleotide.

Thus, the present invention includes polynucleotides encoding the same mature enzyme as shown in FIG. 1 (SEQ ID NO:2) as well as variants of such polynucleotides which variants encode for a fragment, derivative or analog of the enzyme of FIG. 1 (SEQ ID NO:2). Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO: 1). As known in the art, an allelic variant is an alternate form of a polynucleotide sequence which may have a substitution, deletion or addition of one or more nucleotides, which does not substantially alter the function of the encoded enzyme.

The present invention also includes polynucleotides, wherein the coding sequence for the mature enzyme may be fused in the same reading frame to a polynucleotide sequence which aids in expression and secretion of an enzyme from a host cell, for example, a leader sequence which functions to control transport of an enzyme from the cell. The enzyme having a leader sequence is a preprotein and may have the leader sequence cleaved by the host cell to form the mature form of the enzyme. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature enzyme, or for an enzyme having a prosequence or for an enzyme having both a prosequence and a presequence (leader sequence).

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode enzymes which either retain substantially the same biological function or activity as the mature enzyme encoded by the DNA of FIG. 1 (SEQ ID NO: 1).

Alternatively, the polynucleotide may have at least 15 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO: 1, for example, for recovery of the polynucleotide or as a PCR primer.

Thus, the present invention is directed to polynucleotides having at least a 70% identity, preferably at least 90 % identity and more preferably at least a 95 % identity to a polynucleotide which encodes the enzyme of SEQ ID NO:2 as well as fragments thereof, which fragments have at least 30 bases and preferably at least 50 bases and to enzymes encoded by such polynucleotides.

The present invention further relates to a enzyme which has the deduced amino acid sequence of FIG. 1 (SEQ ID NO:2), as well as fragments, analogs and derivatives of such enzyme.

The terms "fragment," "derivative" and "analog" when referring to the enzyme of FIG. 1 (SEQ ID NO:2) means a enzyme which retains essentially the same biological function or activity as such enzyme. Thus, an analog includes a proprotein which can be activated by cleavage of the proprotein portion to produce an active mature enzyme.

The enzyme of the present invention may be a recombinant enzyme, a natural enzyme or a synthetic enzyme, preferably a recombinant enzyme.

The fragment, derivative or analog of the enzyme of FIG. 1 (SEQ ID NO:2) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature enzyme is fused with another compound, such as a compound to increase the half-life of the enzyme (for example, polyethylene glycol), or (iv) one in which the additional amino acids are fused to the mature enzyme, such as a leader or secretory sequence or a sequence which is employed for purification of the mature enzyme or a proprotein sequence. Such fragments, derivatives and analogs are deemed to be within the scope of those skilled in the art from the teachings herein.

The enzymes and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

The enzymes of the present invention include the enzyme of SEQ ID NO:2 (in particular the mature enzyme) as well as enzymes which have at least 70% similarity (preferably at least 70% identity) to the enzyme of SEQ ID NO:2 and more preferably at least 90% similarity (more preferably at least 90% identity) to the enzyme of SEQ ID NO:2 and still more preferably at least 95 % similarity (still more preferably at least 95 % identity) to the enzyme of SEQ ID NO:2 and also include portions of such enzymes with such portion of the enzyme generally containing at least 30 amino acids and more preferably at least 50 amino acids.

As known in the art "similarity" between two enzymes is determined by comparing the amino acid sequence and its conserved amino acid substitutes of one enzyme to the sequence of a second enzyme. Similarity may be determined by procedures which are well-known in the art, for example, a BLAST program (Basic Local Alignment Search Tool at the National Center for Biological Information).

A variant, i.e. a "fragment", "analog" or "derivative" enzyme, and reference enzyme may differ in amino acid sequence by one or more substitutions, additions, deletions, fusions and truncations, which may be present in any combination.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Most highly preferred are variants which retain the same biological function and activity as the reference polypeptide from which it varies.

Fragments or portions of the enzymes of the present invention may be employed for producing the corresponding full-length enzyme by peptide synthesis; therefore, the fragments may be employed as intermediates for producing the full-length enzymes. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of enzymes of the invention by recombinant techniques.

Host cells are genetically engineered (transduced or transformed or transfected) with the vectors containing the polynucleotides of this invention. Such vectors may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing enzymes by recombinant techniques. Thus, for example, the polynucleotide may be included in any one of a variety of expression vectors for expressing an enzyme. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli,* Streptomyces, *Bacillus subtilis;* fungal cells, such as yeast; insect cells such as Drosophila S2 and Spodoptera S*f*9; animal cells such as CHO, COS or Bowes melanoma;

adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBluescript II (Stratagene); pTRC99a, pKK223-3, pDR540, pRIT2T (Pharmacia); Eukaryotic: pXT1, pSG5 (Stratagene) pSVK3, pBPV, pMSG, pSVLSV40 (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the enzymes of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, Cold Spring Harbor, N.Y., (1989), the disclosure of which is hereby incorporated by reference.

Transcription of the DNA encoding the enzymes of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated enzyme. Optionally, the heterologous sequence can encode a fusion enzyme including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The enzymes of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the enzymes of the present invention may be glycosylated or may be non-glycosylated. Enzymes of the invention may or may not also include an initial methionine amino acid residue.

The enzymes, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the enzymes corresponding to a sequence of the present invention can be obtained by direct injection of the enzymes into an animal or by administering the enzymes to an animal, preferably a nonhuman. The antibody so obtained will then bind the enzymes itself. In this manner, even a sequence encoding only a fragment of the enzymes can be used to generate antibodies binding the whole native enzymes. Such antibodies can then be used to isolate the enzyme from cells expressing that enzyme.

For preparation of monoclonal antibodies, any technique which provides antibodies produced by continuous cell line cultures can be used. Examples include the hybridoma technique (Kohler and Milstein, 1975, Nature, 256:495 –497), the trioma technique, the human B-cell hybridoma technique (Kozbor et al., 1983,Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic enzyme products of this invention. Also, transgenic mice may be used to express humanized antibodies to immunogenic enzyme products of this invention.

Antibodies generated against the enzyme of the present invention may be used in screening for similar enzymes from other organisms and samples. Such screening techniques are known in the art, for example, one such screening assay is described in "Methods for Measuring Cellulase Activities", *Methods in Enzymology*, Vol 160, pp. 87–116, which is hereby incorporated by reference in its entirety. Antibodies may also be employed as a probe to screen gene libraries generated from this or other organisms to identify this or cross reactive activities.

The present invention is further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis et al., Id., p. 146). Unless otherwise provided, ligation may be accomplished using known buffers and conditions with 10 units of T4 DNA ligase ("ligase") per 0.5 $\mu$g of approximately equimolar amounts of the DNA fragments to be ligated.

Unless otherwise stated, transformation was performed as described in the method of Sambrook, Fritsch and Maniatus, 1989.

EXAMPLE 1

Bacterial Expression and Purification of Amidase

A Thennococcus GU5L5 genomic library was screened for amidase activity as described in Example 2 and a positive clone was identified and isolated. DNA of this clone was used as a template in a 100 $\mu$l PCR reaction using the following primer sequences: 5' primer: CCGAGAATTC ATTAAAGAGG AGAAATTAAC TATGACCGGC ATCGAATGGA 3' (SEQ ID. NO:3). 3' primer: 5' AATAAGGATC CACACTGGCA CAGTGTCAAG ACA 3' (SEQ ID. NO:4).

The protein was expressed in *E. coli*. The gene was amplified using PCR with the primers indicated above.

Subsequent to amplification, the PCR product was cloned into the EcoRI and BamHI sites of pQET1 and transformed by electroporation into E. coli M15(pREP4). The resulting transformants were grown up in 3 ml cultures, and a portion of this culture was induced. A portion of the uninduced and induced cultures were assayed using Z-L-Phe-AMC (see below).

The primer sequences set out above may also be employed to isolate the target gene from the deposited material by hybridization techniques described above.

EXAMPLE 2

Discovery of an amidase from Thermococcus GU5L5

Production of the expression gene bank.

Colonies containing pBluescript plasmids with random inserts from the organism Thennococcus GU5L5 was obtained according to the method of Hay and Short. (Hay, B. and Short, J., Strategies. 1992, 5, 16.) The resulting colonies were picked with sterile toothpicks and used to singly inoculate each of the wells of 96-well microtiter plates. The wells contained 250 μL of LB media with 100 μg/mL ampicillin, 80 μg/mL methicillin, and 10% v/v glycerol (LB Amp/Meth, glycerol). The cells were grown overnight at 37° C. without shaking. This constituted generation of the "SourceGeneBank"; each well of the Source GeneBank thus contained a stock culture of E. coli cells, each of which contained a pBluescript plasmid with a unique DNA insert.

Screening for amidase activity.

The plates of the Source GeneBank were used to multiply inoculate a single plate (the "Condensed Plate") containing in each well 200 μL of LB Amp/Meth, glycerol. This step was performed using the High Density Replicating Tool (HDRT) of the Beckman Biomek with a 1% bleach, water, isopropanol, air-dry sterilization cycle in between each inoculation. Each well of the Condensed Plate thus contained 10 to 12 different pBluescript clones from each of the source library plates. The Condensed Plate was grown for 16 h at 37° C. and then used to inoculate two white 96-well Polyfiltronics microtiter daughter plates containing in each well 250 μL of LB Amp/Meth (without glycerol). The original condensed plate was put in storage −80° C. The two condensed daughter plates were incubated at 37° C. for 18 h.

The '600 μM substrate stock solution' was prepared as follows: 25 mg of N-morphourea-L-phenylalanyl-7-amido-4-trifluoromethylcoumarin(Mu-Phe-AFC,EnzymeSystems Products, Dublin, Calif.) was dissolved in the appropriate volume of DMSO to yield a 25.2 mM solution. Two hundred fifty microliters of DMSO solution was added to ca. 9 mL of 50 mM, pH 7.5 Hepes buffer containing 0.6 mg/mL of dodecyl maltoside. The volume was taken to 10.5 mL with the above Hepes buffer to yield a cloudy solution.

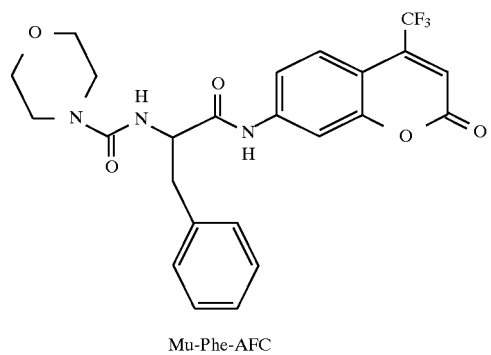

Mu-Phe-AFC

Fifty μL of the '600 ILM stock solution' was added to each of the wells of a white condensed plate using the Biomek to yield a final concentration of substrate of ~100 μM. The fluorescence values were recorded (excitation =400 nm, emission =505 nm) on a plate reading fluorometer immediately after addition of the substrate. The plate was incubated at 70° C. for 60 min. and the fluorescence values were recorded again. The initial and final fluorescence values were subtracted to determine if an active clone was present by an increase in fluorescence over the majority of the other wells. Isolation of the active clone.

In order to isolate the individual clone which carried the activity, the Source GeneBank plates were thawed and the individual wells used to singly inoculate a new plate containing LB Amp/Meth. As above the plate was incubated at 37° C. to grow the cells, and 50 μL of 600 μM substrate stock solution added using the Biomek. Once the active well from the source plate was identified, the cells from the source plate were used to inoculate 3 mL cultures of LB/AMP/Meth, which were grown overnight. The plasmid DNA was isolated from the cultures and utilized for sequencing and construction of expression subdlones.

EXAMPLE 3

Thernococcus GUSL5 Amidase characterization

Substrate specificity.

Using the following substrates (see below for definitions of the abbreviations): CBZ-L-ala-AMC, CBZ-L-arg-AMC, CBZ-L-met-AMC, CBZ-L-phe-AMC, and 7-methylumbelliferyl heptanoate at 100 μM for 1 hour at 70° C. in the assays as described in the clone discovery section, the relative activity of the amidase was 3:3:1:<0.1:<0.1 for the compounds CBZ-L-arg-AMC: CBZ-L-phe-AMC : CBZ-L-met-AMC: CBZ-L-ala-AMC : 7-methylumbelliferyl heptanoate. The excitation and emission wavelengths for the 7-amido-4-methylcoumarins were 380 and 460 nm respectively, and 326 and 450 for the methylumbelliferone.

The abbreviations stand for the following compounds:

CBZ-L-ala-AMC =Nα-carbonylbenzyloxy-L-alanine-7-amido-4-methylcoumarin

CBZ-L-arg-AMC =Nα-carbonylbenzyloxy-L-arginine-7-amido-4-methylcoumarin

CBZ-D-arg-AMC =Nα-carbonylbenzyloxy-D-arginine-7-amido-4-methylcoumarin

CBZ-L-met-AMC =Nα-carbonylbenzyloxy-L-methionine-7-amido-4-methylcoumarin

CBZ-L-phe-AMC =Nα-carbonylbenzyloxy-L-phenylalanine-7-amido-4-methylcoumarin

Organic solvent sensitivity.

Figure 2:
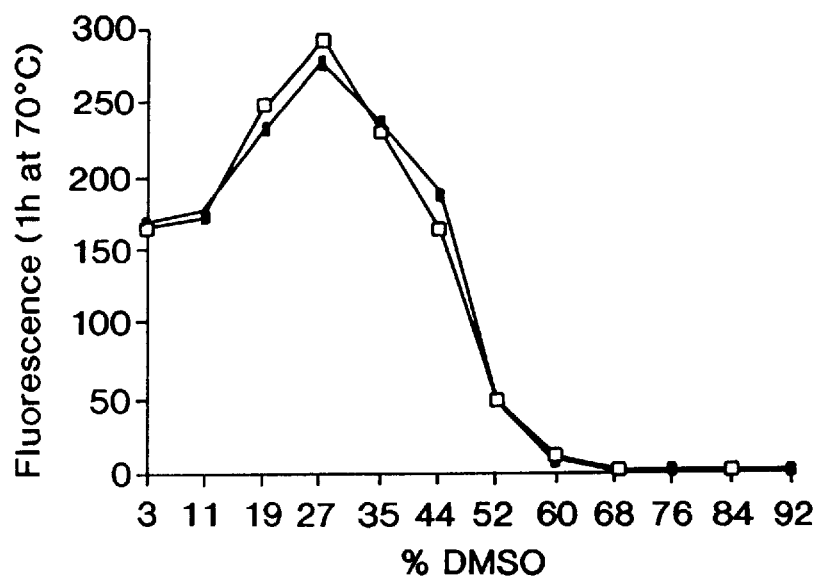
FIG. 2 shows the fluorescence versus concentration of DMSO. The filled and open boxes represent individual assays from Example 3.

The activity of the amidase in increasing concentrations of dimethyl sulfoxide (DMSO) was tested as follows: to each well of a microtiter plate was added 10 μL of 3 mM CBZ-L-phe-AMC in DMSO, 25 μL of cell lysate containing the amidase activity, and 250 μL of a variable mixture of DMSO:pH 7.5, 50 mM Hepes buffer. The reactions were heated for 1 hour at 70° C. and the fluorescence measured. FIG. 2 shows the fluorescence versus concentration of DMSO. The filled and open boxes represent individual assays.

The activity and enantioselectivity of the amidase in increasing concentrations of dimethyl formamide (DMF) was tested as follows: to each well of a microtiter plate was added 30 μL of 1 mM CBZ-L-arg-AMC or CBZ-D-arg-AMC in DMF, 30 μL of cell lysate containing the amidase activity, and 240 μL of a variable mixture of DMF:pH 7.5, 50 mM Hepes buffer. The reactiosn were incubated at RT for 1 hour and the fluorescence measured at 1 minute intervals. FIG. 3 shows the relative initial linear rates (increase in fluorescence per min, i.e., 'activity') versus concentration of DMF for the more reactive CBZ-L-arg-AMC.

The initial linear rate ('activity') of the L and the D CBZ-arg-AMC substrates are shown in Tables 1 and 2 below:

TABLE 1

Activity of the CBZ-D-arg-AMC:

| DMF | Initial Rate, Fl.U./min |
| --- | --- |
| 0.4% | 654 |
| 10% | 2548 |
| 20% | 1451 |
| 30% | 541 |
| 40% | 345 |

TABLE 1-continued

Activity of the CBZ-D-arg-AMC:

| DMF | Initial Rate, Fl.U./min |
| --- | --- |
| 50% | 303 |
| 60% | 190 |
| 75% | 81 |
| 90% | 11 |

TABLE 2

Activity of the CBZ-D-arg-AMC:

| DMF | Initial Rate, Fl.U./min |
| --- | --- |
| 0.4% | 0.3 |
| 10% | 10.1 |
| 20% | 4.6 |
| 30% | 1.8 |
| 40% | 0.9 |
| 50% | 1.2 |
| 60% | 1.4 |
| 75% | 0.1 |
| 90% | 0.1 |

The above data indicate that the enzyme shows excellent selectivity for the L, or 'natural' enantiomer of the derivatized amino acid substrate.

Numerous modifications and variations of the present invention are possible in light of the above teachings and, therefore, within the scope of the appended claims, the invention may be practiced otherwise than as particularly described.

What is claimed is:

1. An isolated polynucleotide sequence encoding a polypeptide of SEQ ID NO:2.

2. An isolated polynucleotide selected from the group consisting of:
   a) SEQ ID NO:1;
   b) SEQ ID NO:1 wherein T can also be U; and
   c) nucleic acid sequences complementary to a) and b).

3. The polynucleotide of claim 1, wherein the polynucleotide is isolated from a prokaryote.

4. An expression vector including the polynucleotide of claim 1.

5. The vector of claim 4, wherein the vector is a plasmid.

6. The vector of claim 4, wherein the vector is virus-derived.

7. A host cell stably transformed with the vector of claim 4.

8. The host cell of claim 7, wherein the cell is a prokaryotic cell.

9. The host cell of claim 7, wherein the cell is a eukaryotic cell.

10. A method for producing a polypeptide comprising:
   a) culturing the host cells of claim 7;
   b) expressing from the host cell of claim 7 a polypeptide encoded by said DNA; and
   c) isolating the polypeptide.

* * * * *

UNITED STATES PATENT AND TRADEMARK OFFICE
CERTIFICATE OF CORRECTION

PATENT NO : 5,877,001
DATED : March 2, 1999
INVENTOR(S): Murphy et al.

It is certified that error appears in the above-identified patent and that said Letters Patent is hereby corrected as shown below:

In SEQ ID NO:1, amino acid number 3, replace the "Tly" with --Gly--.
In SEQ ID NO:1, nucleic acid base numbers 1228 and 1231, replace the "T" with --G--.
In SEQ ID NO:1, nucleic acid base numbers 1229 and 1232, replace the "G" with --T--.

Signed and Sealed this

Eighteenth Day of July, 2000

Attest:

Q. TODD DICKINSON

*Attesting Officer*     *Director of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1869 NUCLEOTIDES
        ( B ) TYPE: NUCLEIC ACID
        ( C ) STRANDEDNESS: SINGLE
        ( D ) TOPOLOGY: LINEAR ( i i ) MOLECULE TYPE: DNA ( x i ) SEQUENCE DESCRIPTION: SEQ ID NO:1:

```
ATG  ACC  GGC  ATC  GAA  TGG  AAC  CAC  GAG  ACC  TTT  TCT  AAG  TTC  GCC  TAC         48
Met  Thr  Tly  Ile  Glu  Trp  Asn  His  Glu  Thr  Phe  Ser  Lys  Phe  Ala  Tyr
                    5                        10                       15

CTG  GGC  GAC  CCG  AGG  ATA  CGG  GGA  AAC  TTA  ATC  GCG  TAC  ACC  CTG  ACG         96
Leu  Gly  Asp  Pro  Arg  Ile  Arg  Gly  Asn  Leu  Ile  Ala  Tyr  Thr  Leu  Thr
                    20                       25                       30

AAG  GCC  AAC  ATG  AAG  GAC  AAC  AAG  TAC  GAG  AGC  ACG  GTT  GTT  GTT  GAA        144
Lys  Ala  Asn  Met  Lys  Asp  Asn  Lys  Tyr  Glu  Ser  Thr  Val  Val  Val  Glu
                    35                       40                       45

GAC  CTT  GAA  ACG  GGC  TCA  AGG  CGC  TTC  ATC  GAG  AAC  GCC  TCA  ATG  CCG        192
Asp  Leu  Glu  Thr  Gly  Ser  Arg  Arg  Phe  Ile  Glu  Asn  Ala  Ser  Met  Pro
```

```
                50                          55                          60
AGG  ATT  TCG  CCA  GAC  GGC  AGA  AAG  CTC  GCC  TTC  ACC  TGC  TTT  AAC  GAG      240
Arg  Ile  Ser  Pro  Asp  Gly  Arg  Lys  Leu  Ala  Phe  Thr  Cys  Phe  Asn  Glu
65             70                            75                           80

GAG  AAG  AAG  GAG  ACC  GAG  ATA  TGG  GTG  GCC  GAT  ATC  CAG  ACC  CTG  AGC      288
Glu  Lys  Lys  Glu  Thr  Glu  Ile  Trp  Val  Ala  Asp  Ile  Gln  Thr  Leu  Ser
                         85                            90                       95

GCC  AAG  AAA  GTC  CTC  TCA  ACT  AAA  AAC  GTC  CGC  TCG  ATG  CAG  TGG  AAC      336
Ala  Lys  Lys  Val  Leu  Ser  Thr  Lys  Asn  Val  Arg  Ser  Met  Gln  Trp  Asn
              100                          105                      110

GAC  GAT  TCA  AGG  AGA  CTC  TTA  GTT  GTC  GGC  TTC  AAG  AGG  AGG  GAC  GAT      384
Asp  Asp  Ser  Arg  Arg  Leu  Leu  Val  Val  Gly  Phe  Lys  Arg  Arg  Asp  Asp
              115                          120                      125

GAG  GAC  TTC  GTC  TTT  GAC  GAC  GAC  GTC  CCG  GTC  TGG  TTC  GAC  AAT  ATG      432
Glu  Asp  Phe  Val  Phe  Asp  Asp  Asp  Val  Pro  Val  Trp  Phe  Asp  Asn  Met
         130                          135                      140

GGA  TTC  TTT  GAT  GGA  GAG  AAG  ACG  ACG  TTC  TGG  GTT  CTT  GAC  ACT  GAG      480
Gly  Phe  Phe  Asp  Gly  Glu  Lys  Thr  Thr  Phe  Trp  Val  Leu  Asp  Thr  Glu
145                     150                          155                      160

GCC  GAG  GAG  ATA  ATC  GAG  CAG  TTC  GAG  AAG  CCG  AGG  TTT  TCG  AGT  GGC      528
Ala  Glu  Glu  Ile  Ile  Glu  Gln  Phe  Glu  Lys  Pro  Arg  Phe  Ser  Ser  Gly
                    165                          170                      175

CTC  TGG  CAC  GGC  GAT  GCG  ATA  GTT  GTG  AAC  GTC  CCG  CAC  CGC  GAG  GGG      576
Leu  Trp  His  Gly  Asp  Ala  Ile  Val  Val  Asn  Val  Pro  His  Arg  Glu  Gly
              180                          185                      190

AGC  AAG  CCT  GCC  CTG  TTC  AAG  TTC  TAC  GAC  ATA  GTC  CTA  TGG  AAG  GAC      624
Ser  Lys  Pro  Ala  Leu  Phe  Lys  Phe  Tyr  Asp  Ile  Val  Leu  Trp  Lys  Asp
         195                          200                      205

GGG  GAG  GAA  GAG  AAG  CTC  TTC  GAG  AGG  GTC  TCC  TTC  GAG  GCG  GTT  GAC      672
Gly  Glu  Glu  Glu  Lys  Leu  Phe  Glu  Arg  Val  Ser  Phe  Glu  Ala  Val  Asp
210                     215                          220

TCC  GAC  GGA  AAG  AGA  ATA  CTC  CTG  AGG  GGC  AAG  AAA  AAG  CGG  TTC          720
Ser  Asp  Gly  Lys  Arg  Ile  Leu  Leu  Arg  Gly  Lys  Lys  Lys  Arg  Phe
225                     230                          235                      240

ATC  AGC  GAG  CAC  GAC  TGG  CTG  TAC  CTC  TGG  GAC  GGC  GAG  CTT  AAA  CCG      768
Ile  Ser  Glu  His  Asp  Trp  Leu  Tyr  Leu  Trp  Asp  Gly  Glu  Leu  Lys  Pro
              245                          250                      255

ATC  TAC  GAG  GGC  CCG  CTC  GAC  GTC  TGG  GAA  GCC  AAG  CTC  ACG  GAA  GGA      816
Ile  Tyr  Glu  Gly  Pro  Leu  Asp  Val  Trp  Glu  Ala  Lys  Leu  Thr  Glu  Gly
         260                          265                      270

AAG  GTC  TAC  TTC  CTC  ACT  CCA  GAT  GCG  GGC  AGG  GTA  AAC  CTC  TGG  CTC      864
Lys  Val  Tyr  Phe  Leu  Thr  Pro  Asp  Ala  Gly  Arg  Val  Asn  Leu  Trp  Leu
         275                          280                      285

TGG  GAC  GGG  AAG  GCC  GAG  CGT  GTT  GTT  ACC  GGC  GAC  CAC  TGG  ATT  TAC      912
Trp  Asp  Gly  Lys  Ala  Glu  Arg  Val  Val  Thr  Gly  Asp  His  Trp  Ile  Tyr
290                     295                          300

GGG  CTT  GAC  GTC  AGC  GAT  GGC  AAA  GCA  TTG  CTC  CTC  ATC  ATG  ACC  GCC      960
Gly  Leu  Asp  Val  Ser  Asp  Gly  Lys  Ala  Leu  Leu  Leu  Ile  Met  Thr  Ala
305                     310                          315                      320

ACG  AGG  ATA  GGC  GAG  CTC  TAC  CTC  TAC  GAC  GGC  GAG  CTG  AAA  CAG  GTC     1008
Thr  Arg  Ile  Gly  Glu  Leu  Tyr  Leu  Tyr  Asp  Gly  Glu  Leu  Lys  Gln  Val
                    325                          330                      335

ACC  GAA  TAC  AAC  GGG  CCG  ATA  TTC  AGG  AAG  CTC  AAG  ACC  TTC  GAG  CCG     1056
Thr  Glu  Tyr  Asn  Gly  Pro  Ile  Phe  Arg  Lys  Leu  Lys  Thr  Phe  Glu  Pro
              340                          345                      350

AGG  CAC  TTC  CGC  TTC  AAG  AGC  AAA  GAC  CTC  GAG  ATA  GAC  GGC  TGG  TAC     1104
Arg  His  Phe  Arg  Phe  Lys  Ser  Lys  Asp  Leu  Glu  Ile  Asp  Gly  Trp  Tyr
         355                          360                      365

CTC  AGG  CCG  GAG  GTT  AAA  GAG  GAG  AAG  GCC  CCG  GTG  ATA  GTC  TTC  GTC     1152
Leu  Arg  Pro  Glu  Val  Lys  Glu  Glu  Lys  Ala  Pro  Val  Ile  Val  Phe  Val
```

-continued

```
                  370                           375                             380
CAC  GGC  GGG  CCG  AAG  GGC  ATG  TAC  GGA  CAC  CGC  TTC  GTC  TAC  GAG  ATG        1200
His  Gly  Gly  Pro  Lys  Gly  Met  Tyr  Gly  His  Arg  Phe  Val  Tyr  Glu  Met
385                 390                      395                           400

CAG  CTG  ATG  GCG  AGC  AAG  GGC  TAC  TAC  TGC  TGC  TTC  GTG  AAC  CCG  CGC        1248
Gln  Leu  Met  Ala  Ser  Lys  Gly  Tyr  Tyr  Val  Val  Phe  Val  Asn  Pro  Arg
                    405                      410                      415

GGC  AGC  GAC  GGC  TAT  AGC  GAA  GAC  TTC  GCG  CTC  CGC  GTC  CTG  GAG  AGG        1296
Gly  Ser  Asp  Gly  Tyr  Ser  Glu  Asp  Phe  Ala  Leu  Arg  Val  Leu  Glu  Arg
               420                      425                      430

ACT  GGC  TTG  GAG  GAC  TTT  GAG  GAC  ATA  ATG  AAC  GGC  ATC  GAG  GAG  TTC        1344
Thr  Gly  Leu  Glu  Asp  Phe  Glu  Asp  Ile  Met  Asn  Gly  Ile  Glu  Glu  Phe
          435                      440                      445

TTC  AAG  CTC  GAA  CCG  CAG  GCC  GAC  AGG  GAG  CGC  GTT  GGA  ATA  ACG  GGC        1392
Phe  Lys  Leu  Glu  Pro  Gln  Ala  Asp  Arg  Glu  Arg  Val  Gly  Ile  Thr  Gly
     450                      455                      460

ATA  AGC  TAC  GGC  GGC  TTC  ATG  ACC  AAC  TGG  GCC  TTG  ACT  CAG  AGC  GAC        1440
Ile  Ser  Tyr  Gly  Gly  Phe  Met  Thr  Asn  Trp  Ala  Leu  Thr  Gln  Ser  Asp
465                      470                      475                      480

CTC  TTC  AAG  GCA  GGA  ATA  AGC  GAG  AAC  GGC  ATA  AGC  TAC  TGG  CTC  ACC        1488
Leu  Phe  Lys  Ala  Gly  Ile  Ser  Glu  Asn  Gly  Ile  Ser  Tyr  Trp  Leu  Thr
                    485                      490                      495

AGC  TAC  GCC  TTC  TCG  GAC  ATA  GGG  CTC  TGG  TAC  GAC  GTC  GAG  GTC  ATC        1536
Ser  Tyr  Ala  Phe  Ser  Asp  Ile  Gly  Leu  Trp  Tyr  Asp  Val  Glu  Val  Ile
               500                      505                      510

GGG  CCA  AAT  CCG  TTA  GAG  AAC  GAG  AAC  TTC  AGG  AAG  CTC  AGC  CCG  CTG        1584
Gly  Pro  Asn  Pro  Leu  Glu  Asn  Glu  Asn  Phe  Arg  Lys  Leu  Ser  Pro  Leu
          515                      520                      525

TTC  TAC  GCT  CAG  AAC  GTG  AAG  GCG  CCG  ATA  CTC  CTA  ATC  CAC  TCG  CTT        1632
Phe  Tyr  Ala  Gln  Asn  Val  Lys  Ala  Pro  Ile  Leu  Leu  Ile  His  Ser  Leu
     530                      535                      540

GAG  GAC  TAC  CGC  TGT  CCG  CTC  GAC  CAG  AGC  CTT  ATG  TTC  TAC  AAC  GTG        1680
Glu  Asp  Tyr  Arg  Cys  Pro  Leu  Asp  Gln  Ser  Leu  Met  Phe  Tyr  Asn  Val
545                      550                      555                      560

CTC  AAG  GAC  ATG  GGC  AAG  GAA  GCC  TAC  ATA  GCG  ATA  TTC  AAG  CGC  GGC        1728
Leu  Lys  Asp  Met  Gly  Lys  Glu  Ala  Tyr  Ile  Ala  Ile  Phe  Lys  Arg  Gly
565                      570                      575

GCC  CAC  GGC  CAC  AGC  GTC  CGC  GGA  AGC  CCG  AGG  CAC  AGG  CCG  AAG  CGC        1776
Ala  His  Gly  His  Ser  Val  Arg  Gly  Ser  Pro  Arg  His  Arg  Pro  Lys  Arg
580                      585                      590

TAC  AGG  CTC  TTC  ATA  GAG  TTC  TTC  GAG  CGC  AAG  CTC  AAG  AAG  TAC  GAG        1824
Tyr  Arg  Leu  Phe  Ile  Glu  Phe  Phe  Glu  Arg  Lys  Leu  Lys  Lys  Tyr  Glu
595                      600                      605

GAG  GGC  TTT  GAG  GTA  GAG  AAG  ATA  CTC  AAG  GGG  AAT  GGG  AAC  TGA             1869
Glu  Gly  Phe  Glu  Val  Glu  Lys  Ile  Leu  Lys  Gly  Asn  Gly  Asn
610                      615                      620
```

( 2 ) INFORMATION FOR SEQ ID NO:2:

( i ) SEQUENCE CHARACTERISTICS:
        ( A ) LENGTH: 622 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:2:

```
Met  Thr  Gly  Ile  Glu  Trp  Asn  His  Glu  Thr  Phe  Ser  Lys  Phe  Ala  Tyr
                    5                        10                       15

Leu  Gly  Asp  Pro  Arg  Ile  Arg  Gly  Asn  Leu  Ile  Ala  Tyr  Thr  Leu  Thr
                    20                       25                       30
```

```
Lys Ala Asn Met Lys Asp Asn Lys Tyr Glu Ser Thr Val Val Glu
         35                  40                 45

Asp Leu Glu Thr Gly Ser Arg Arg Phe Ile Glu Asn Ala Ser Met Pro
     50                  55                 60

Arg Ile Ser Pro Asp Gly Arg Lys Leu Ala Phe Thr Cys Phe Asn Glu
65              70                 75                       80

Glu Lys Lys Glu Thr Glu Ile Trp Val Ala Asp Ile Gln Thr Leu Ser
                85                 90                     95

Ala Lys Lys Val Leu Ser Thr Lys Asn Val Arg Ser Met Gln Trp Asn
            100             105             110

Asp Asp Ser Arg Arg Leu Leu Val Val Gly Phe Lys Arg Arg Asp Asp
            115             120             125

Glu Asp Phe Val Phe Asp Asp Val Pro Val Trp Phe Asp Asn Met
        130             135             140

Gly Phe Phe Asp Gly Glu Lys Thr Thr Phe Trp Val Leu Asp Thr Glu
145             150             155                     160

Ala Glu Glu Ile Ile Glu Gln Phe Glu Lys Pro Arg Phe Ser Ser Gly
                165             170             175

Leu Trp His Gly Asp Ala Ile Val Val Asn Val Pro His Arg Glu Gly
            180             185             190

Ser Lys Pro Ala Leu Phe Lys Phe Tyr Asp Ile Val Leu Trp Lys Asp
        195             200             205

Gly Glu Glu Glu Lys Leu Phe Glu Arg Val Ser Phe Glu Ala Val Asp
    210             215             220

Ser Asp Gly Lys Arg Ile Leu Leu Arg Gly Lys Lys Lys Lys Arg Phe
225             230             235                     240

Ile Ser Glu His Asp Trp Leu Tyr Leu Trp Asp Gly Glu Leu Lys Pro
                245             250             255

Ile Tyr Glu Gly Pro Leu Asp Val Trp Glu Ala Lys Leu Thr Glu Gly
            260             265             270

Lys Val Tyr Phe Leu Thr Pro Asp Ala Gly Arg Val Asn Leu Trp Leu
        275             280             285

Trp Asp Gly Lys Ala Glu Arg Val Val Thr Gly Asp His Trp Ile Tyr
    290             295             300

Gly Leu Asp Val Ser Asp Gly Lys Ala Leu Leu Leu Ile Met Thr Ala
305             310             315                     320

Thr Arg Ile Gly Glu Leu Tyr Leu Tyr Asp Gly Glu Leu Lys Gln Val
                325             330             335

Thr Glu Tyr Asn Gly Pro Ile Phe Arg Lys Leu Lys Thr Phe Glu Pro
            340             345             350

Arg His Phe Arg Phe Lys Ser Lys Asp Leu Glu Ile Asp Gly Trp Tyr
        355             360             365

Leu Arg Pro Glu Val Lys Glu Lys Ala Pro Val Ile Val Phe Val
    370             375             380

His Gly Gly Pro Lys Gly Met Tyr Gly His Arg Phe Val Tyr Glu Met
385             390             395                     400

Gln Leu Met Ala Ser Lys Gly Tyr Tyr Val Val Phe Val Asn Pro Arg
            405             410             415

Gly Ser Asp Gly Tyr Ser Glu Asp Phe Ala Leu Arg Val Leu Glu Arg
        420             425             430

Thr Gly Leu Glu Asp Phe Glu Asp Ile Met Asn Gly Ile Glu Glu Phe
    435             440             445

Phe Lys Leu Glu Pro Gln Ala Asp Arg Glu Arg Val Gly Ile Thr Gly
```

-continued

```
                450                              455                              460
Ile  Ser  Tyr  Gly  Gly  Phe  Met  Thr  Asn  Trp  Ala  Leu  Thr  Gln  Ser  Asp
465                      470                      475                           480

Leu  Phe  Lys  Ala  Gly  Ile  Ser  Glu  Asn  Gly  Ile  Ser  Tyr  Trp  Leu  Thr
                    485                      490                          495

Ser  Tyr  Ala  Phe  Ser  Asp  Ile  Gly  Leu  Trp  Tyr  Asp  Val  Glu  Val  Ile
                500                      505                      510

Gly  Pro  Asn  Pro  Leu  Glu  Asn  Glu  Asn  Phe  Arg  Lys  Leu  Ser  Pro  Leu
          515                      520                          525

Phe  Tyr  Ala  Gln  Asn  Val  Lys  Ala  Pro  Ile  Leu  Leu  Ile  His  Ser  Leu
          530                    535                      540

Glu  Asp  Tyr  Arg  Cys  Pro  Leu  Asp  Gln  Ser  Leu  Met  Phe  Tyr  Asn  Val
545                      550                      555                           560

Leu  Lys  Asp  Met  Gly  Lys  Glu  Ala  Tyr  Ile  Ala  Ile  Phe  Lys  Arg  Gly
                565                      570                          575

Ala  His  Gly  His  Ser  Val  Arg  Gly  Ser  Pro  Arg  His  Arg  Pro  Lys  Arg
               580                    585                          590

Tyr  Arg  Leu  Phe  Ile  Glu  Phe  Phe  Glu  Arg  Lys  Leu  Lys  Lys  Tyr  Glu
          595                      600                      605

Glu  Gly  Phe  Glu  Val  Glu  Lys  Ile  Leu  Lys  Gly  Asn  Gly  Asn
     610                    615                      620
```

( 2 ) INFORMATION FOR SEQ ID NO:3:

( i ) SEQUENCE CHARACTERISTICS:
    ( A ) LENGTH: 50 NUCLEOTIDES
    ( B ) TYPE: NUCLEIC ACID
    ( C ) STRANDEDNESS: SINGLE
    ( D ) TOPOLOGY: LINEAR ( i i ) MOLECULE TYPE: Oligonucleotide ( x i ) SEQUENCE DESCRIPTION: SEQ ID NO:3:

CCGAGAATTC ATTAAAGAGG AGAAATTAAC TATGACCGGC ATCGAATGGA       50

( 2 ) INFORMATION FOR SEQ ID NO:4:

( i ) SEQUENCE CHARACTERISTICS:
    ( A ) LENGTH: 33 NUCLEOTIDES
    ( B ) TYPE: NUCLEIC ACID
    ( C ) STRANDEDNESS: SINGLE
    ( D ) TOPOLOGY: LINEAR ( i i ) MOLECULE TYPE: Oligonucleotide ( x i ) SEQUENCE DESCRIPTION: SEQ ID NO:4:

AATAAGGATC CACACTGGCA CAGTGTCAAG ACA       33